US012799441B2

(12) United States Patent
Jeong et al.

(10) Patent No.: US 12,799,441 B2
(45) Date of Patent: Nov. 17, 2026

(54) ORGANOID CULTURE DEVICE AND ORGANOID CULTURE METHOD USING THE SAME

(71) Applicant: INJE UNIVERSITY INDUSTRY-ACADEMIC COOPERATION FOUNDATION, Gimhae-si (KR)

(72) Inventors: Se Hoon Jeong, Gimhae-si (KR); Soo Min Lee, Gimhae-si (KR)

(73) Assignee: INJE UNIVERSITY INDUSTRY-ACADEMIC COOPERATION FOUNDATION, Gimhae-si (KR)

( * ) Notice: Subject to any disclaimer, the term of this patent is extended or adjusted under 35 U.S.C. 154(b) by 368 days.

(21) Appl. No.: 18/432,112

(22) Filed: Feb. 5, 2024

(65) Prior Publication Data

US 2024/0228923 A1 Jul. 11, 2024

Related U.S. Application Data

(63) Continuation of application No. PCT/KR2022/010508, filed on Jul. 19, 2022.

(30) Foreign Application Priority Data

Aug. 10, 2021 (KR) ........................ 10-2021-0104948

(51) Int. Cl.

| | |
|---|---|
| ***C12M 1/00*** | (2006.01) |
| ***C12M 1/32*** | (2006.01) |
| ***C12M 1/34*** | (2006.01) |
| ***C12M 3/00*** | (2006.01) |

(52) U.S. Cl.

CPC ............ *C12M 21/08* (2013.01); *C12M 23/12* (2013.01); *C12M 23/38* (2013.01); *C12M 29/26* (2013.01); *C12M 41/12* (2013.01); *C12N 2513/00* (2013.01)

(58) Field of Classification Search

CPC ......... B32B 37/142; C12M 1/00; C12M 1/02; C12M 1/12; C12M 1/32; C12M 21/08; C12M 23/12; C12M 23/38; C12M 29/26; C12M 3/00; C12M 41/12; C12N 2513/00

See application file for complete search history.

(56) References Cited

U.S. PATENT DOCUMENTS

| | | | | |
|---|---|---|---|---|
| 2017/0198245 | A1 | 7/2017 | Oh et al. | |
| 2021/0055283 | A1* | 2/2021 | Collins | C12M 41/48 |
| 2021/0087515 | A1* | 3/2021 | Allbritton | C12M 25/04 |

FOREIGN PATENT DOCUMENTS

| | | | |
|---|---|---|---|
| KR | 101437147 | B1 | 9/2014 |
| KR | 20150051199 | A | 5/2015 |
| KR | 20160125997 | A | 11/2016 |

(Continued)

*Primary Examiner* — Lydia Edwards

(74) *Attorney, Agent, or Firm* — NKL Law; Jae Youn Kim

(57) ABSTRACT

A culture device for manufacturing an organoid of a 3D shape according to an embodiment includes: a culture plate provided with one or more insertion grooves; and an organoid device inserted to and removed from the insertion grooves and provided with one or more culture grooves, wherein the culture grooves provided on the culture plate may be formed in a pattern having a predetermined diameter on the surface of the culture plate.

7 Claims, 15 Drawing Sheets

(56) References Cited

FOREIGN PATENT DOCUMENTS

| | | | |
|---|---|---|---|
| KR | 20190086549 | A | 7/2019 |
| KR | 102187633 | B1 | 12/2020 |
| KR | 20210043968 | A | 4/2021 |
| WO | 2021153837 | A1 | 8/2021 |

* cited by examiner

ORGANOID CULTURE DEVICE AND ORGANOID CULTURE METHOD USING THE SAME

TECHNICAL FIELD

The present invention relates to an organoid culture device used to culture organoids of a 3D shape and an organoid culture method using the same. More specifically, it relates to an organoid culture device which is easier to use than the conventional organoid culture devices and which allows for culture of organoids of a uniform shape, and an organoid culture method using the same.

BACKGROUND ART

Cell culture is a technology for cultivating cells isolated from an individual outside of the individual, and the key issue of cell culture is to consistently maintain a culture environment that is created to be similar to the inside of the individual.

Regarding the key issue, as technology develops today, various cell culture methods are being proposed.

Among these, in the traditionally used cell culture method, monolayer cells that are thinly spread in a two-dimensional direction are cultured, but this has a problem that the cells are unable to maintain for a long time their specific functions that the cells originally have in vivo.

Therefore, recently, the culture of organoids, which are three-dimensional tissues with functions equivalent to those in vivo, has been attracting attention, and a variety of three-dimensional organoid culture technologies are currently being developed.

However, even in these various three-dimensional organoid culture technologies, there is a problem that since the organoid culture is tiny, when a medium is replaced while the organoid is contained in a predetermined plate, it is highly probable that it is lost.

This is because a medium is generally removed using a vacuum pump. Not only because it is very inconvenient and difficult to replace a medium while visually confirming a tiny organoid, but also because workers experience a high level of fatigue, there are additional problems such as delay of research schedule and deterioration of workers' health.

Accordingly, there is an urgent need to develop a technology regarding an organoid culture device and an organoid culture method using the same in order to solve the problems described above.

Technical Problem

The object of an organoid culture device and an organoid culture method using the same according to an embodiment of the present invention is to provide an organoid culture device which is easier to use than the conventional organoid culture devices and which allows for culture of organoids of a uniform shape, and an organoid culture method using the same.

Technical Solution

An organoid culture device according to an embodiment of the present invention designed to solve the above problems is an organoid culture device used to culture organoids in a 3D shape, and it includes: a culture plate provided with one or more insertion grooves; and an organoid device inserted to and removed from each of the insertion grooves and provided with one or more culture grooves, wherein the culture grooves provided on the organoid device are formed on a surface of the organoid device in a pattern having a diameter of 5 μm to 5000 μm and spaced apart from each other in 5 μm to 5000 μm.

In addition, below each of the insertion grooves, a first air injection port may be provided to discharge an organoid device out of each of the insertion grooves by supplying air in a direction of the inserted organoid device.

In addition, below each of the culture grooves, a second air injection port is provided to discharge an organoid out of each of the culture grooves by delivering air in a direction of the organoid after receiving air from the first air injection port.

In addition, a heating means for generating heat may be provided inside the culture plate along an outer circumference of each of the insertion grooves.

In addition, an organoid culture device according to an embodiment of the present invention may further include a protective cover protecting the organoids seated and cultured in the culture grooves from external shocks or foreign substances, wherein the protective cover is provided to be detachable from or attachable to an upper portion of the culture plate or to rotate about a point or an axis of the culture plate, thereby operating to selectively open or seal the upper portion of the culture plate.

Here, the protective cover may include: a first air conditioning flow path provided vertically on an inner wall of the protective cover to allow a cooling means or a heating means to flow therein; and a second air conditioning flow path provided on an inner ceiling of the protective cover to allow the cooling means or the heating means to flow therein.

In addition, an organoid culture device according to an embodiment of the present invention may further include: a measurement portion measuring a critical state inside the protective cover; and an input/output device receiving the critical state measured by the measurement portion, displaying the same to a user, and receiving an input value from the user.

Meanwhile, an organoid culture method for culturing the organoids in a 3D shape, using the culture device according to an embodiment of the present invention may include: an injection step of injecting cells into the one or more culture grooves provided in the organoid device; a culture step of culturing the cells by inserting the organoid device into an insertion groove provided on the culture plate; and a completion step of discharging the cultured organoids to the outside of the one or more culture grooves after the culturing is completed.

Advantageous Effects

An organoid culture device and an organoid culture method using the same according to an embodiment of the present invention are easier to use than the conventional organoid culture devices and allow for culture of organoids of a uniform shape.

In addition, an organoid culture device according to an embodiment of the present invention has an advantage that it can collect organoids by easily discharging them from a culture groove without a separate collection device for extracting organoids that have been completely cultured or it can remove an organoid device itself from an insertion groove.

In addition, an organoid culture device according to an embodiment of the present invention has an advantage of protecting an organoid being cultured in an organoid device from external shocks or foreign substances by covering an upper portion of the organoid device.

Here, since devices required for a user to culture an organoid are provided inside and outside the protective cover, there is an advantage that no separate organoid management device is required.

DETAILED DESCRIPTION OF THE INVENTION

Figure 1:
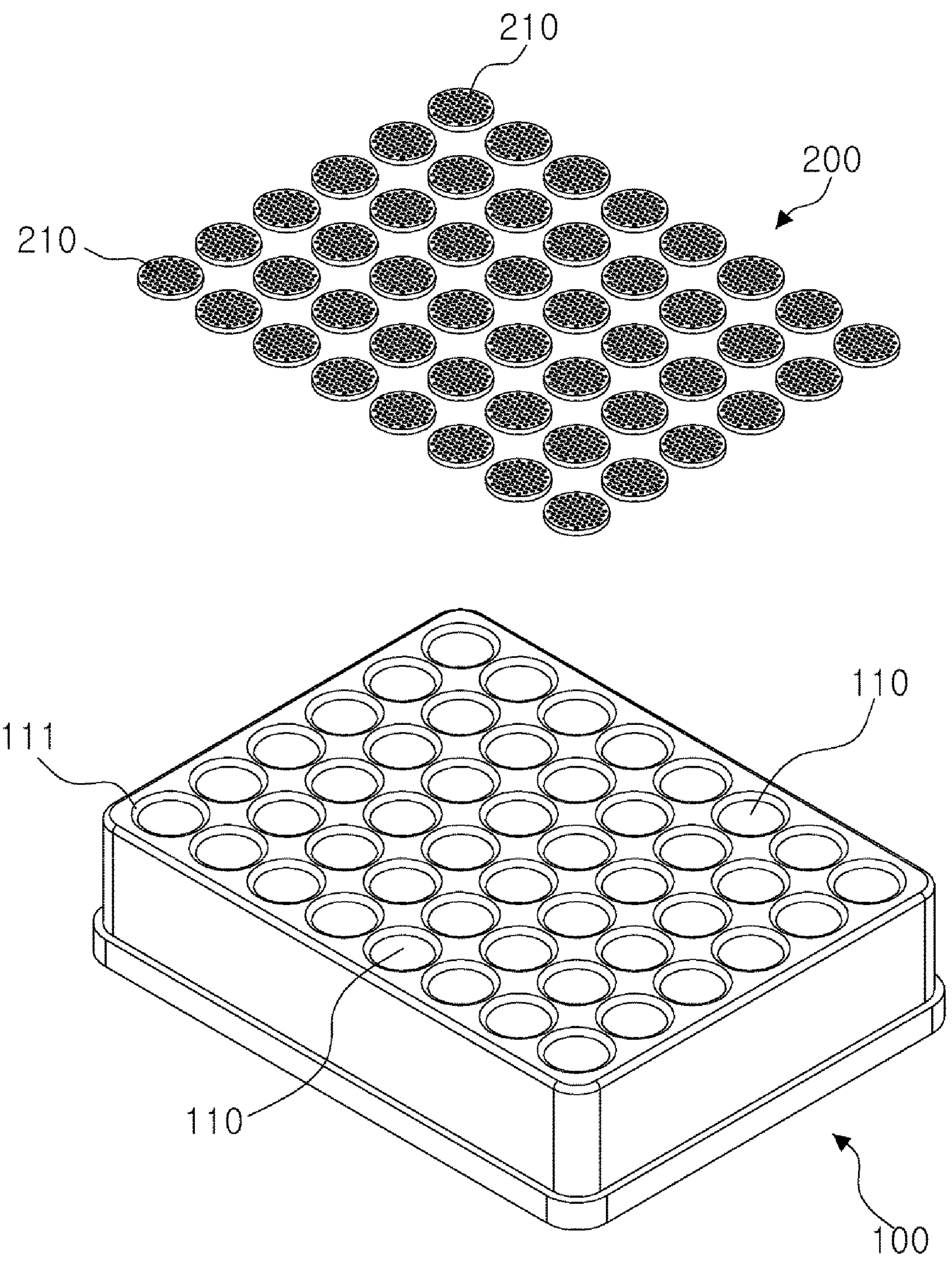
FIG. 1 is an exemplary diagram of an organoid culture device according to an embodiment of the present invention.

An organoid culture device according to an embodiment of the present invention, which is an organoid culture device used to culture an organoids of a 3D shape, may include: a culture plate provided with one or more insertion grooves; and an organoid device inserted to and removed from the insertion groove and provided with one or more culture grooves, wherein the culture grooves provided on the organoid device are formed on a surface of the organoid device in a pattern having a diameter of 5 μm to 5000 μm each in a spacing of 5 μm to 5000 μm, and a culture method using the same may include: an injection step of injecting cells into a culture groove provided in an organoid device; a culture step of culturing cells by inserting an organoid device into an insertion groove provided on a culture plate; and a completion step of discharging a cultured organoid to the outside of the culture groove after culture is completed.

Hereinafter, the detailed description of the present invention with reference to the drawings is not limited to specific embodiments, and various changes may be made and various embodiments may be possible. In addition, the content described below should be understood to include all conversions, equivalents, and substituents included in the spirit and technical scope of the present invention.

In the description below, terms such as "first" and "second," etc., are terms used to describe various components, such components must not be limited to the above terms. The above terms are used only to distinguish one component from another.

Same reference numerals used throughout the present specification refer to same elements.

An expression used in the singular encompasses the expression of the plural, unless it has a clearly different meaning in the context. In addition, it is to be understood that terms used below such as "including" or "having," etc. are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Unless defined otherwise, all terms used herein, including technical or scientific terms, have the same meaning as commonly understood by one of ordinary skill in the art to which the present invention belongs. Terms such as those defined in commonly used dictionaries should be interpreted as having a meaning consistent with the meaning in the context of the related art, and are not interpreted in an ideal or excessively formal sense unless explicitly defined in the present application.

In addition, In providing descriptions referring to the accompanying drawings, those components that are the same are rendered the same reference numeral regardless of the figure number, and redundant descriptions are omitted. In the description of the present invention, when it is determined that the detailed description of the related art would obscure the gist of the present invention, the detailed description thereof will be omitted.

Hereinafter, a 3D shaped organoid culture device 1 and an organoid culture method using the same according to an embodiment of the present invention will be described in detail with reference to FIGS. 1 to 16 attached to an embodiment of the present invention.

Figure 2:
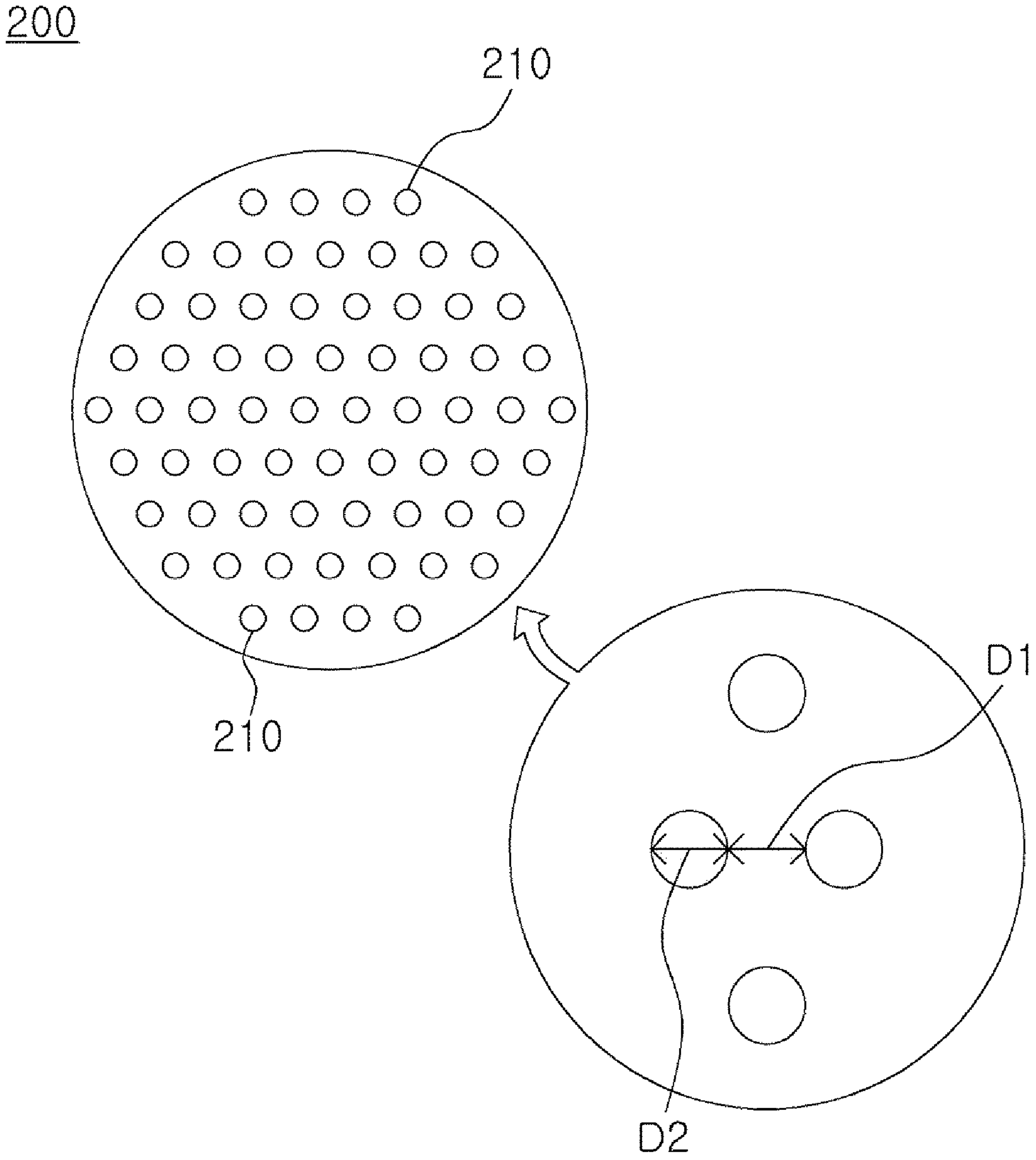
FIG. 2 is an exemplary floor diagram showing a spacing between culture grooves and a diameter of the culture grooves provided in an organoid device.

FIG. 1 is an exemplary diagram of an organoid culture device according to an embodiment of the present invention; FIG. 2 is an exemplary floor diagram showing a spacing between culture grooves and a diameter of the culture grooves provided in an organoid device; and FIG. 16 is an exemplary diagram showing an organoid of a 3D shape cultured through an organoid culture device according to an embodiment of the present invention.

Figure 16:
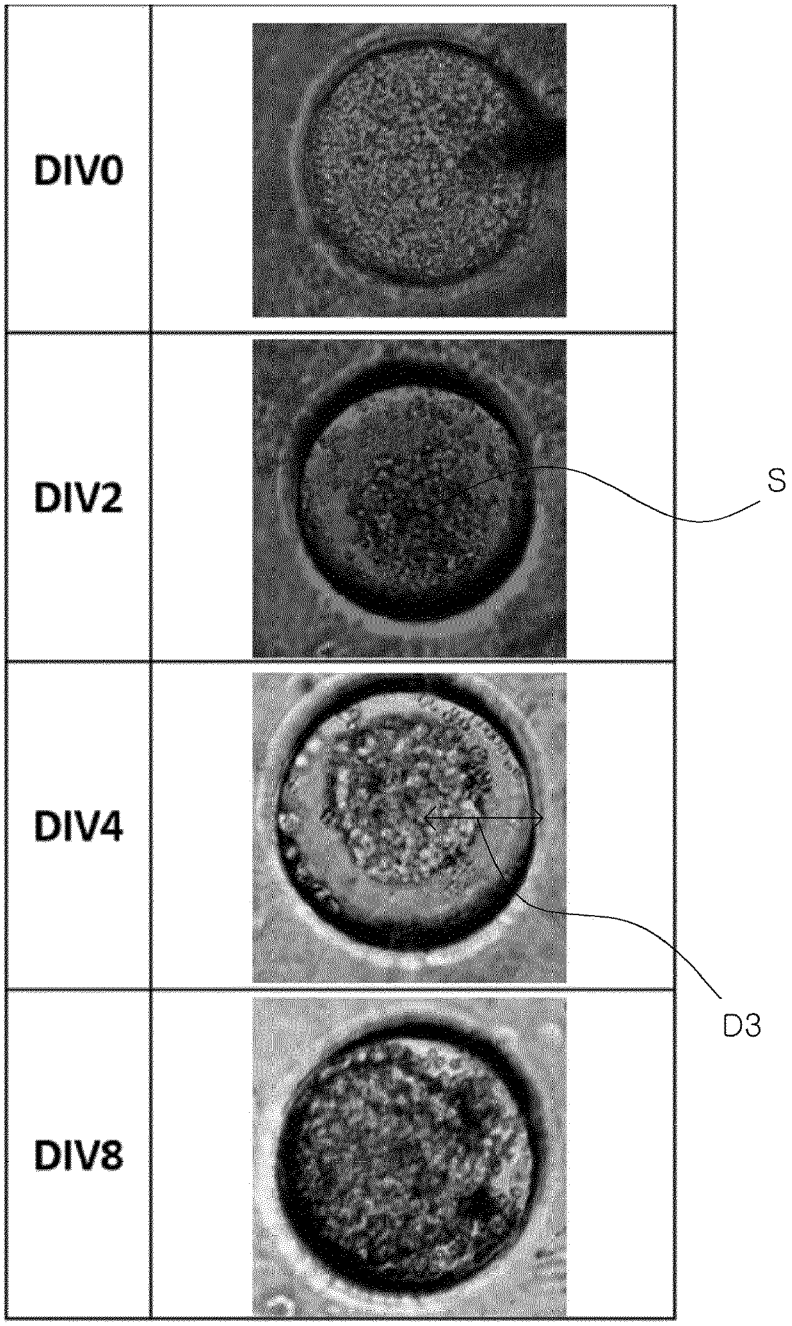
FIG. 16 is an exemplary diagram showing an organoid of a 3D shape cultured through an organoid culture device and an organoid culture method using the same according to an embodiment of the present invention.

Referring to FIGS. 1, 2, and 16, an organoid culture device 1 according to an embodiment of the present invention is an organoid culture device with the purpose of culturing an organoid (S) of a 3D shape, and it may include a culture plate 100 and an organoid device 200.

First, the culture plate 100 may be formed to have a rectangular cross-section and a predetermined height as illustrated in FIG. 1, so that it may ultimately be prepared to have the shape of a rectangular box.

At this time, the shape of the culture plate 100 may preferably be a shape of a rectangular box, but this is only an example of the shape. It may be provided in the shape of a cylindrical shape having a circular cross-section with a predetermined height, or in the shape of a polygonal pillar having a polygonal cross-section such as a triangle and a pentagon with a predetermined height.

In addition, a slip prevention member may be provided below the culture plate 100 to prevent slipping, and the slip prevention member may be made of a synthetic resin with a high friction coefficient such as rubber or urethane.

Accordingly, a culture plate 100 according to an embodiment of the present invention may form a fixing force on a fixing surface of a table or installation mount in a laboratory where the present invention is installed.

In addition, one or more insertion grooves 110 may be provided on an upper portion of the culture plate 100, and at this time, the shape of the insertion groove 110 may be provided such that the cross-section forms a circular shape.

In addition, the insertion groove 110 may be provided in a penetrated state forming a predetermined depth in a direction from the top of a culture plate 100 to the bottom of the culture plate 100, and most preferably, the insertion groove 110 may be provided in a state where the culture plate 100 is penetrated to a height of the middle.

At this time, when the depth of the insertion groove 110 is too shallow, a problem may occur in which an organoid device 200, which will be described in detail later, is too easily separated from the insertion groove 110 of the culture plate 100, and when the depth of the insertion groove 110 is too deep, a problem may occur in which it is difficult for a user to take the organoid device 200 out of the insertion groove 110. Therefore, in order to solve these problems, the depth of the insertion groove 110 may be provided to have a depth down to the middle of the culture plate 100.

In addition, an insertion guide 111 having a gently curved cross-section to form a constant radius may be provided on an edge of an outer circumferential surface of the insertion groove 110.

In this way, when an edge of an outer circumferential surface of the insertion groove 110 forms a predetermined radius, it may smoothly guide the insertion of an organoid device 200, which will be described later, and thus there is an advantage that a user can more easily insert the organoid device to the insertion groove 110 and remove the same therefrom.

In addition, insertion grooves 110 provided in the culture plate 100 may be formed to have a rectangular arrangement, most preferably, a square arrangement.

In addition, on an outer edge of the culture plate 100, in order to indicate the position of an insertion groove 110 to a user, matrix tables displaying letters (A, B, C) in the horizontal direction of the edges of the culture plate 100 and Arabic number (1, 2, 3) in the vertical direction of the edges of the culture plate 100 may be provided in a constant spacing. Through this, there is an advantage that a user who uses the present invention can accurately understand the position of an organoid device inserted into the insertion groove 110.

In addition, the organoid device 200 may be provided to have an overall shape of a disk with a predetermined thickness so that it can be fitted into the insertion groove 110 formed to have a circular cross-section.

Here, the organoid device 200 may be formed through semiconductor processing steps including soft bake, exposure, post exposure bake (PEB), and development steps. The semiconductor process here refers to a semiconductor process performed through a wafer processing, an oxidation process, a photolithography process, an etching process, a thin film process, a metal wiring process, and an EDS process. Hereinafter, the semiconductor process steps will be described.

First, in a soft bake process, a wafer raw material for forming an organoid device 200 is primarily baked at a temperature of about 30° C. to 200° C. for about 2 to 48 hours.

Next, an exposure step is a step in which a pattern is formed on a wafer by radiating ultraviolet rays (UV) having a power ranging from 2 W to 200 W to the wafer for about 15 to 25 minutes.

Next, in a post exposure bake (PEB) process step, which is performed after the exposure step is completed, the wafer on which a pattern has been formed is baked at 50° C. to 120° C. within about 7 hours.

Afterwards, the exposed wafer is put into an SU-8 developer solution and shaken slowly for about 30 to 90 minutes.

Next, a special coating is applied onto the completed wafer for 6 to 24 hours to prepare a PDMS mold to be easily removed later.

Subsequently, a step may be performed in which PDMS prepared at a ratio of 1:10 is poured onto the wafer, vacuum treated for about 5 to 60 minutes, left in an oven for about 1 to 12 hours, and then used to make devices one by one using a cutting punch.

In addition, one or more culture grooves 210 may be provided on a surface of the organoid device 200 for culturing an organoid S by inputting a cell culture medium.

Here, as a cell culture medium put into the organoid device 200, any cells used to culture an organoid S, such as primary cell line, continuous cell line, stem cells, tumor cells, immunocytes, bacteria, and microorganisms, may be used.

In addition, the organoid device 200 may be provided to be inserted to and removed from an insertion groove 110 provided on the culture plate 100.

Specifically, the culture groove 210 provided in the organoid device 200 may be formed in a circular pattern having a diameter D2 of 5 μm to 5000 μm in each spacing D1 of 5 μm to 5000 μm on a surface of the organoid device 200 formed in the shape of a disk, and most preferably, it may be provided to form a spacing D1 of 200 μm while having a diameter D2 of 200 μm.

Here, when the spacing D2 of the culture grooves 210 is less than 5 μm, due to the culture grooves 210 being formed at an excessively close distance, individual extraction of organoid S objects inserted into each culture groove 210 is difficult, and at the same time, it is difficult to easily control each organoid (S) after removing an organoid device 200 from the insertion groove 110. In addition, when the spacing exceeds 5000 μm, as an excessively wide spacing is formed, a problem may occur in which efficient operation of an organoid device 200 is impossible. Therefore, the spacing of the culture grooves 210 is preferably provided to maintain a spacing of 5 μm to 5000 μm.

In addition, when the diameter D2 of the culture groove 210 is formed to be less than 5 μm, an organoid (S) cultured in the culture groove 210 is cultured in an excessively small state, and thus a problem may occur in which a user may not easily use an organoid S cultured by using the prevent invention. When the diameter exceeds 5000 μm, due to the excessively wide diameter, an organoid (S) cultured through the present invention may not be smoothly provided with nutrients for maintaining a 3D shape. Therefore, the diameter D2 of the culture groove 210 is preferably formed to maintain a diameter of 5 μm to 5000 μm in order to effectively culture the 3D organoid (S). In addition, when described with the example shown in FIG. 14, the radius D3 formed by the culture groove 210 may be formed to have a length of 2.5 μm to 2500 μm.

In addition, the depth of the culture groove 210 may be formed to have a depth of 5 μm to 5000 μm corresponding to the diameter D2 of the culture groove 210, and this is to culture an organoid of a 3D shape forming a spherical shape.

If the diameter D2 of the culture groove 210 is excessively smaller than the depth of the culture groove 210, the 3D organoid may be formed in the shape of a rugby ball which is convex up and down, and if the diameter D2 of the culture groove 210 is excessively wider than the depth of the culture groove 210, an organoid cultured in the culture groove 210 may be cultured in a the shape of a disk spreading widely laterally rather than in a spherical shape. Therefore, the depth and diameter D2 of the culture groove 210 may preferably have the same length and depth values.

Meanwhile, the organoid device 200 may be formed of a material of polydimethylsiloxane (PDMS), and the polydimethylsiloxane (PDMS) has the advantages of thermal stability, high resistance to ultraviolet rays, and excellent insulation performance.

However, the polydimethylsiloxane (PDMS) is simply the most preferred material for making the organoid device 200, and a variety of polymers may be used to make the organoid device 200, which may be formed of wax, Teflon, photoresists, polytetrafluoroethylene, silicone, metal nanoparticles, metal oxide nanoparticles, silica nanoparticles, polymer nanoparticles, or a combination thereof.

To describe the method for forming the organoid device 200 in more detail, the organoid device 200 may be formed through a heating step.

First, the heating step may be performed through a processing of heating a raw material for forming the organoid device 200, that is, polydimethylsiloxane (PDMS), at a temperature of 50 to 90° C. for 2 to 24 hours.

At this time, when the heating step is performed at a temperature of less than 50° C. and for a time of less than 2 hours, a polydimethylsiloxane (PDMS) raw material used to fabricate an organoid device 200 is not heated at an appropriate temperature and for an appropriate time, and as a result, it is difficult to clearly form a pattern of culture grooves 210 on the surface of the polydimethylsiloxane (PDMS) raw material. When the heating step is performed at a temperature higher than 90° C. and for a time exceeding 24 hours, due to exposure to heat at an excessively high temperature for an excessively long time, deformation may occur in the polydimethylsiloxane (PDMS) raw material. Therefore, the heating step may be preferably performed at a temperature of 50 to 90° C. for 2 to 24 hours.

Meanwhile, the critical numerical values (temperature, time, Watt) described in the process of describing the heating step are simply the most desirable critical numerical values for fabricating an organoid device 200 made of polydimethylsiloxane (PDMS), and it may be performed using various critical numerical values depending on the material forming an organoid device 200.

Accordingly, an organoid culture device 1 according to an embodiment of the present invention has an advantage that it is easier to use than the conventional organoid culture devices and it can allow for culturing of organoids having a uniform 3D shape.

Figure 3:
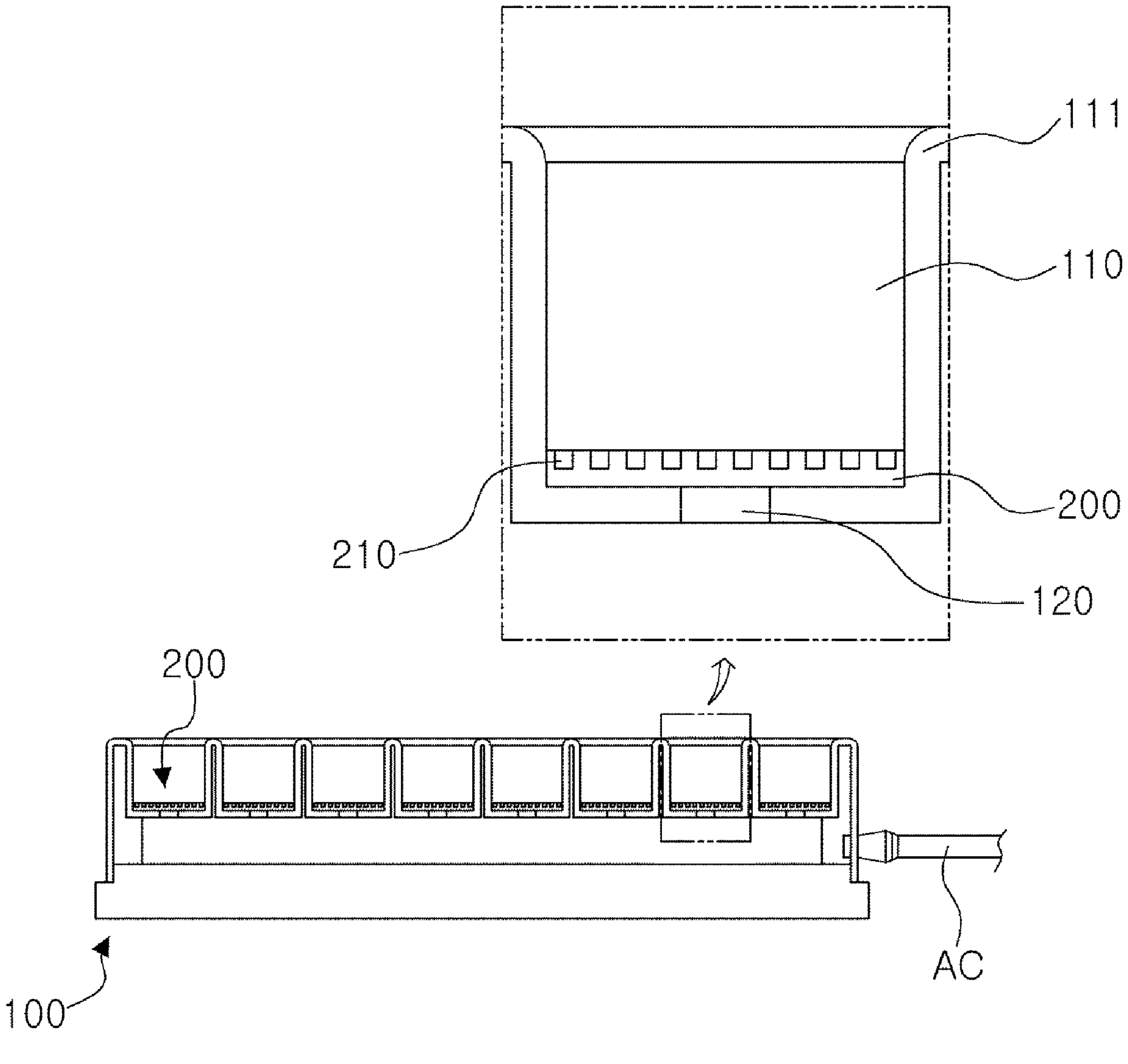
FIG. 3 is a lateral cross-sectional diagram of a culture plate, showing an insertion groove where a first air injection port is provided.

FIG. 3 is a lateral cross-sectional diagram of a culture plate, showing an insertion groove where a first air injection port is provided.

Referring to FIG. 3, as described above, an organoid device 200 according to an embodiment of the present invention may be provided in a shape that may be fitted into an insertion groove 110 by being formed to form a shape corresponding to the circular shape formed by the insertion groove.

For example, when an insertion groove 110 according to an embodiment of the present invention is formed in a circular shape and is formed to have a diameter of a maximum length of 1 CM, an organoid device 200 may also be formed in a circular shape and it may be formed to have a diameter of a maximum length of 0.95 CM to less than 1 CM.

At this time, when the diameter of the insertion groove 110 and the diameter of the organoid device 200 are formed to have exactly the same diameter, the user may undergo difficulties in inserting the organoid device 200 into the insertion groove 110 or in removing the same therefrom. Therefore, a minimum tolerance may be provided between the insertion groove 110 and the organoid device 200 so that fitting may be easily performed.

In addition, on an inner lower side of an insertion groove 110 according to an embodiment of the present invention, provided is a first air injection port 120 discharging an organoid device 200 from an insertion groove 110 by spraying air in a direction of an inserted organoid device 200.

At this time, as shown in FIG. 3, in the inside the culture plate 100, a hollow portion forming a predetermined space may be provided to receive air from a lower side of an organoid device 200.

In addition, at the bottom of the culture plate 100, provided is an air supply means AC supplying air in a direction of a first air injection port 120 by supplying air to a hollow portion provided inside a culture plate 100.

Accordingly, an organoid culture device 1 according to an embodiment of the present invention has an advantage of easier operation, because an organoid device 200 inserted into an insertion groove 110 may be easily removed out of a culture plate 100 by using the pneumatic pressure of air supplied through a first air injection port 120.

Figure 4:
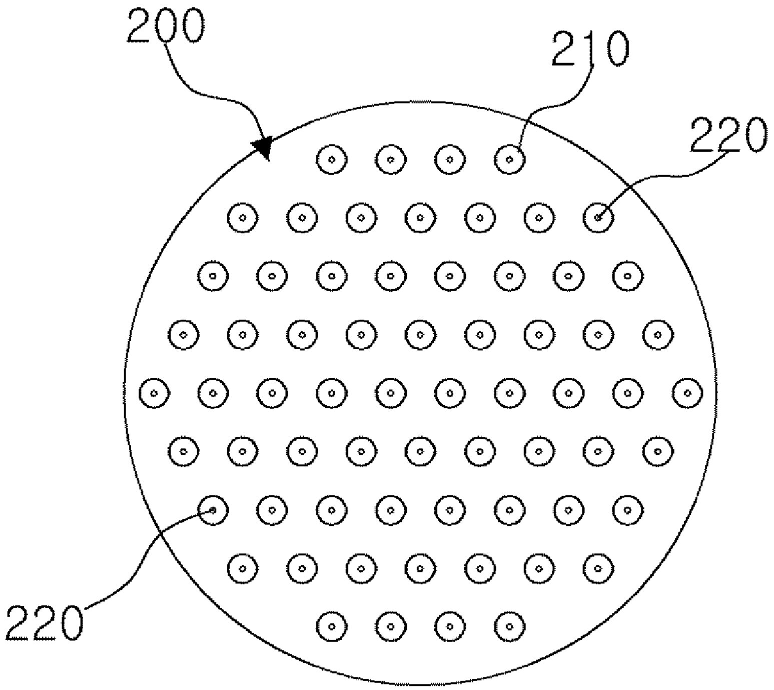
FIG. 4 is an exemplary floor diagram showing a culture plate provided with a second air injection port.
Figure 5:
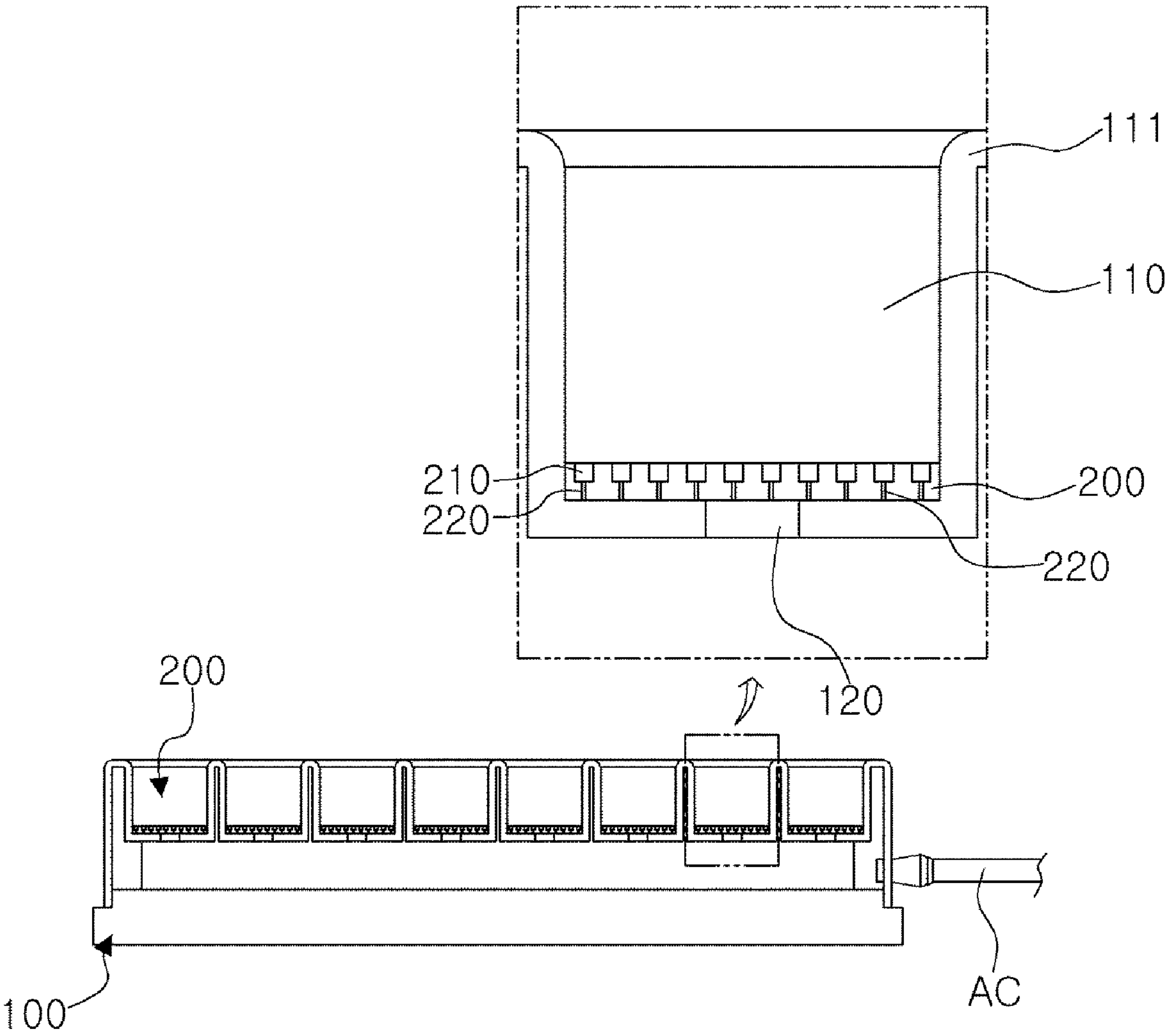
FIG. 5 is a lateral cross-sectional diagram of a culture plate provided with a second air injection port together with a first air injection port.
Figure 6:
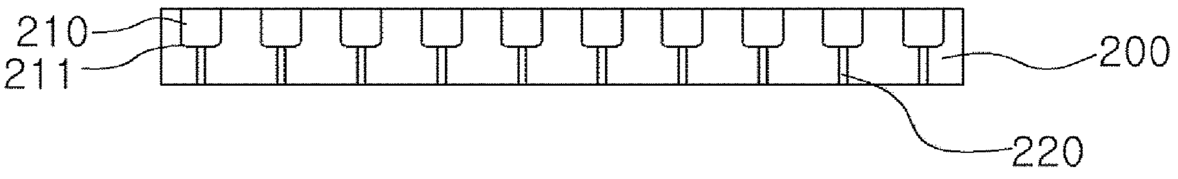
FIG. 6 is an exemplary diagram showing an inner edge of a culture groove formed gently.
Figure 7:
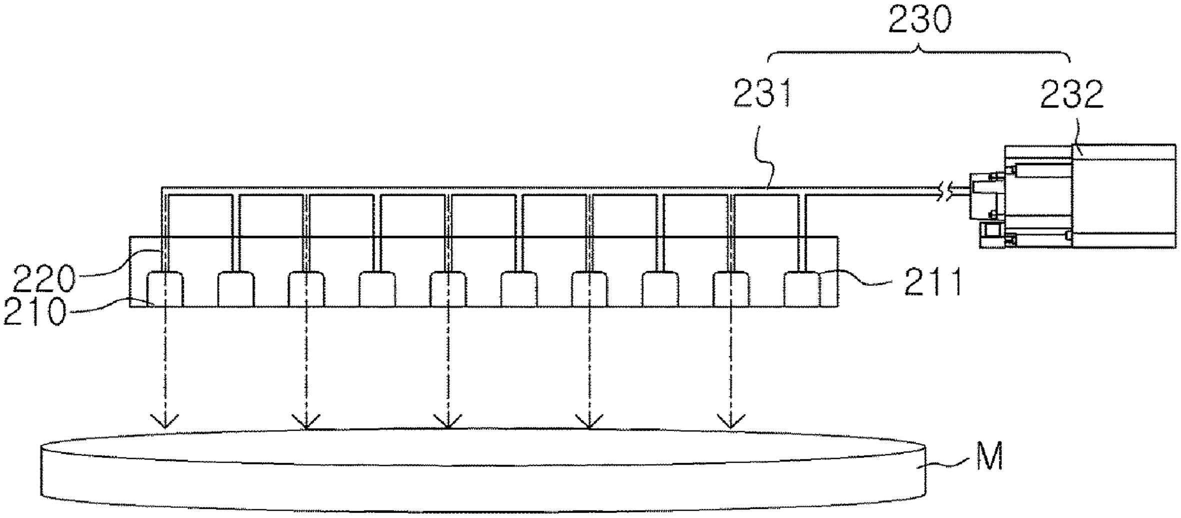
FIG. 7 is an exemplary diagram showing an organoid being discharged by using a pneumatic delivery means.

FIG. 4 is an exemplary floor diagram showing a culture plate provided with a second air injection port; FIG. 5 is a lateral cross-sectional diagram of a culture plate provided with a second air injection port together with a first air injection port; FIG. 6 is an exemplary diagram showing an inner edge of a culture groove formed gently; and FIG. 7 is an exemplary diagram showing an organoid being discharged by using a pneumatic delivery means.

Referring to FIGS. 4 to 7, on an inner lower side of a culture groove 210 according to an embodiment of the present invention, provided is a second air injection port 220 discharging an organoid S from a culture groove 210 by supplying air in a direction of the organoid S being cultured in the culture groove 210.

More specifically, the second air injection port 220 may be operated to discharge an organoid which is being cultured or which has been completely cultured to the outside by supplying air in a direction of the organoid being cultured in a culture groove 210 after receiving the air supplied through a first air injection port 120, which has received the air supplied from the air supply means AC described above.

In addition, referring to FIG. 6, a curved portion 211 may be provided at a lower edge form in the culture groove 210 so that the edge has a gentle shape, and in this way, the culture groove 210 provided to have an edge with a gentle inner side has an advantage that an organoid can be positioned on the central radius of the culture groove 210 to be cultured more easily and that the organoid S can be discharged more easily.

Accordingly, an organoid culture device 1 according to an embodiment of the present invention has an advantage that it can easily collect organoids S from culture grooves 210 without a separate collection device for extracting organoids S that have been completely cultured.

In addition, FIG. 7 is an exemplary diagram showing an organoid being discharged by using a pneumatic delivery means.

Referring to FIG. 7, an organoid culture device 1 according to an embodiment of the present invention may further include a pneumatic pressure delivery means 230 capable of discharging organoids S that have been completely cultured, by supplying air to the second air injection port 220 described above.

Specifically, the pneumatic delivery means 230 may be formed through a combination of features of an air hose 231, which may be directly inserted into the second air injection port 220 described above, and an air compressor 232 which supplies air to the air hose 231.

As a use example to describe an embodiment of the present invention, first, after culturing of an organoid (S) in a culture groove 210 is completed, in a state in which a user has removed an organoid device 200 from a culture plate 100 and turned over the organoid device 200 removed out, by inserting an air hose 231 to a second air injection port 220 and then injection air to the second air injection port 220 using an air compressor 232, the organoid S may be discharged by pneumatic pressure downward, that is, in a direction of a separate collection device for collecting organoids S or of a medium M.

Through this, an organoid culture device 1 according to an embodiment of the present invention has an advantage that organoids S can be discharged from culture grooves 210 more reliably by directly applying pressure to the organoids that have been cultured completely.

Figure 8:
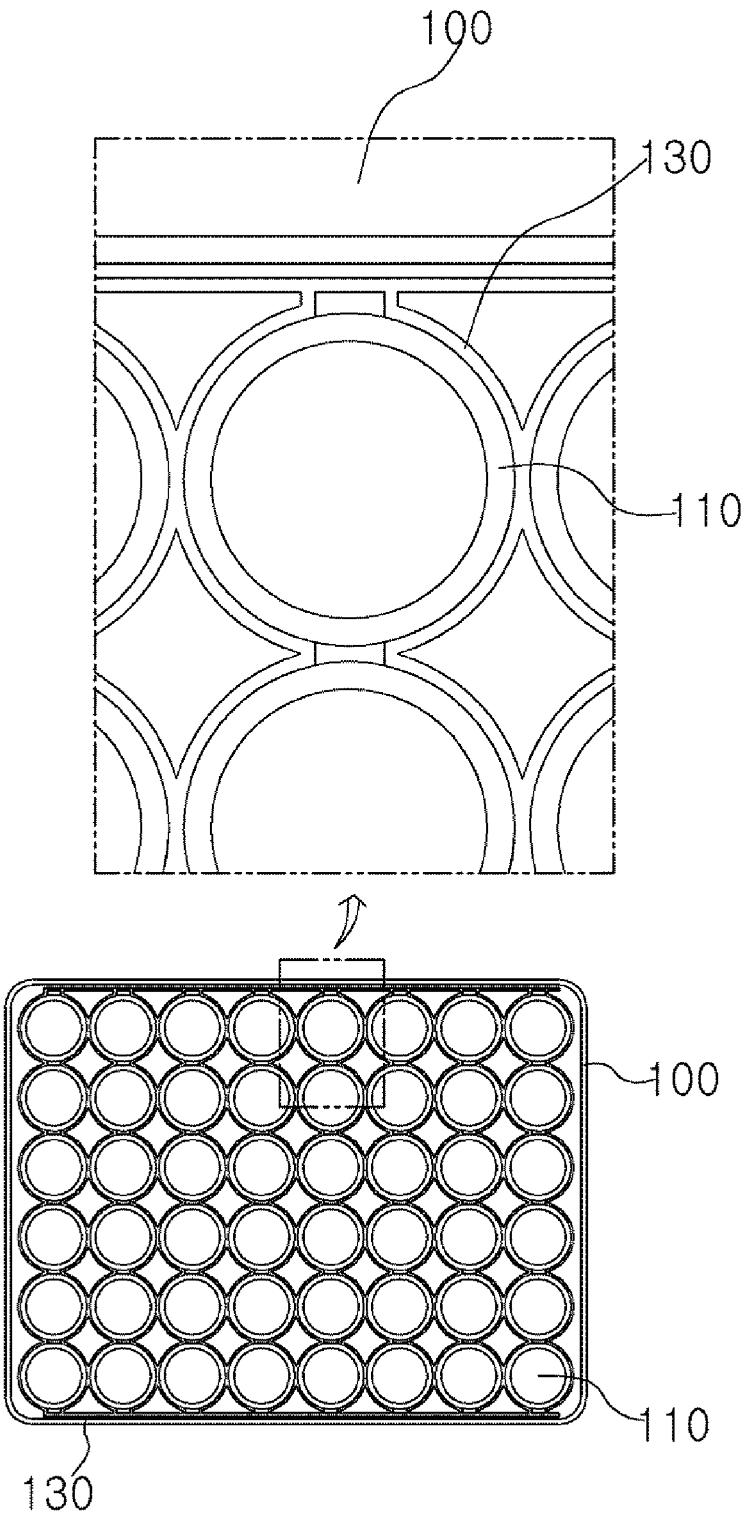
FIG. 8 is exemplary projection diagram of a culture plate provided with a heating means.

In addition, FIG. 8 is exemplary projection diagram of a culture plate provided with a heating means.

Referring to FIG. 8, in the inside of a culture plate 100 according to an embodiment of the present invention, a heating means 130 generating heat by receiving electricity may be provided.

Specifically, the heating means 130 may provided to surround an edge of the outer circumference of the previously described insertion groove 110 and at the same time, it may be formed to have a repeating pattern to surround other insertion grooves 110, thereby having an overall waveform.

At this time, the heating means 130 may be provided inside an organoid device 200, but when the heating means 130 is provided directly inside the organoid device 200 made of a polydimethylsiloxane (PDMS) material, heat conduction is not easy and also the properties of the polydimethylsiloxane (PDMS) material may be modified by heat. In addition, when heat is directly applied to organoids S cultured in a culture groove 210, disruption may occur in culturing organoids S. Therefore, the heating means 130 may be preferably operated on a culture plate 100 so that only indirect heat may be applied to organoids S. Here, the heating means 130 may be an electric heater, an air heater, and a radiator, but not limited thereto, and any heating system that can be appreciated by one of ordinary skill in the art may be applicable.

Accordingly, an organoid culture device 1 according to an embodiment of the present invention has an advantage that it allows to perform the culture of organoids S more efficiently by indirectly applying heat to organoids S being cultured in culture grooves 210 of the organoid device 200.

Figure 9:
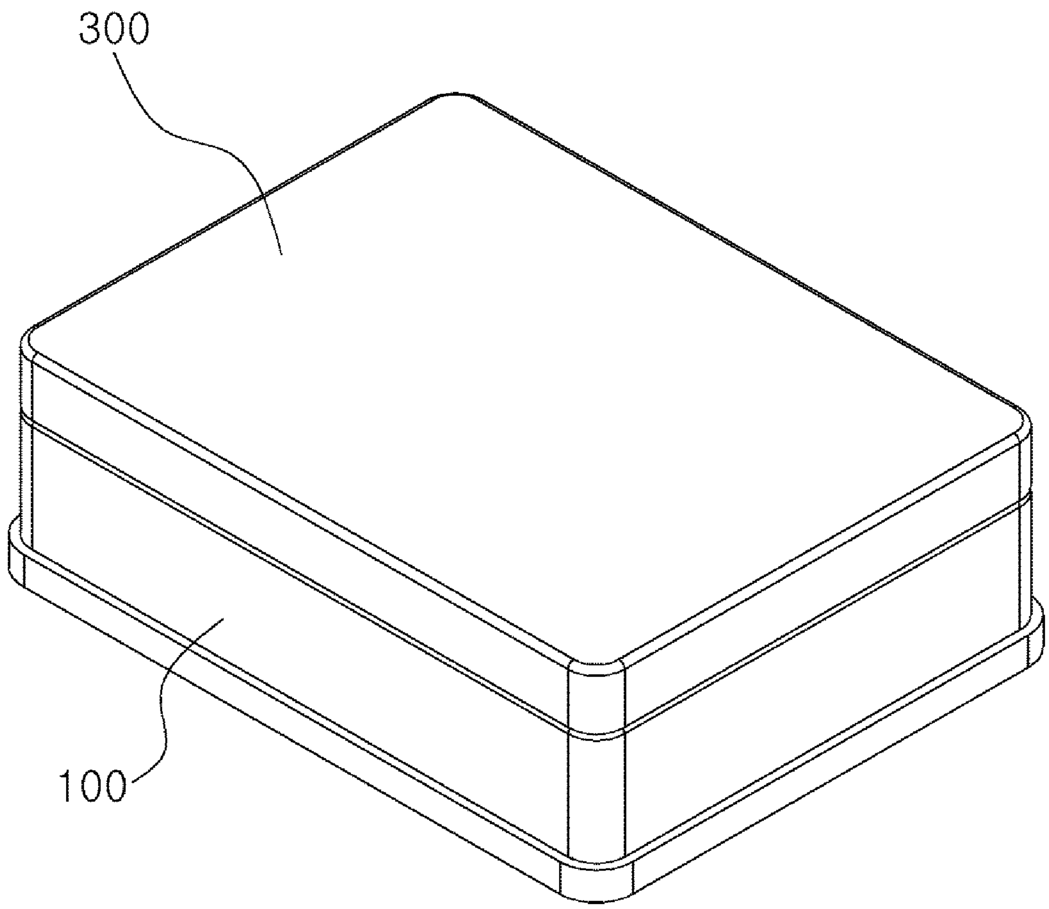
FIG. 9 is an exemplary diagram of an organoid culture device provided with a protective cover.
Figure 10:
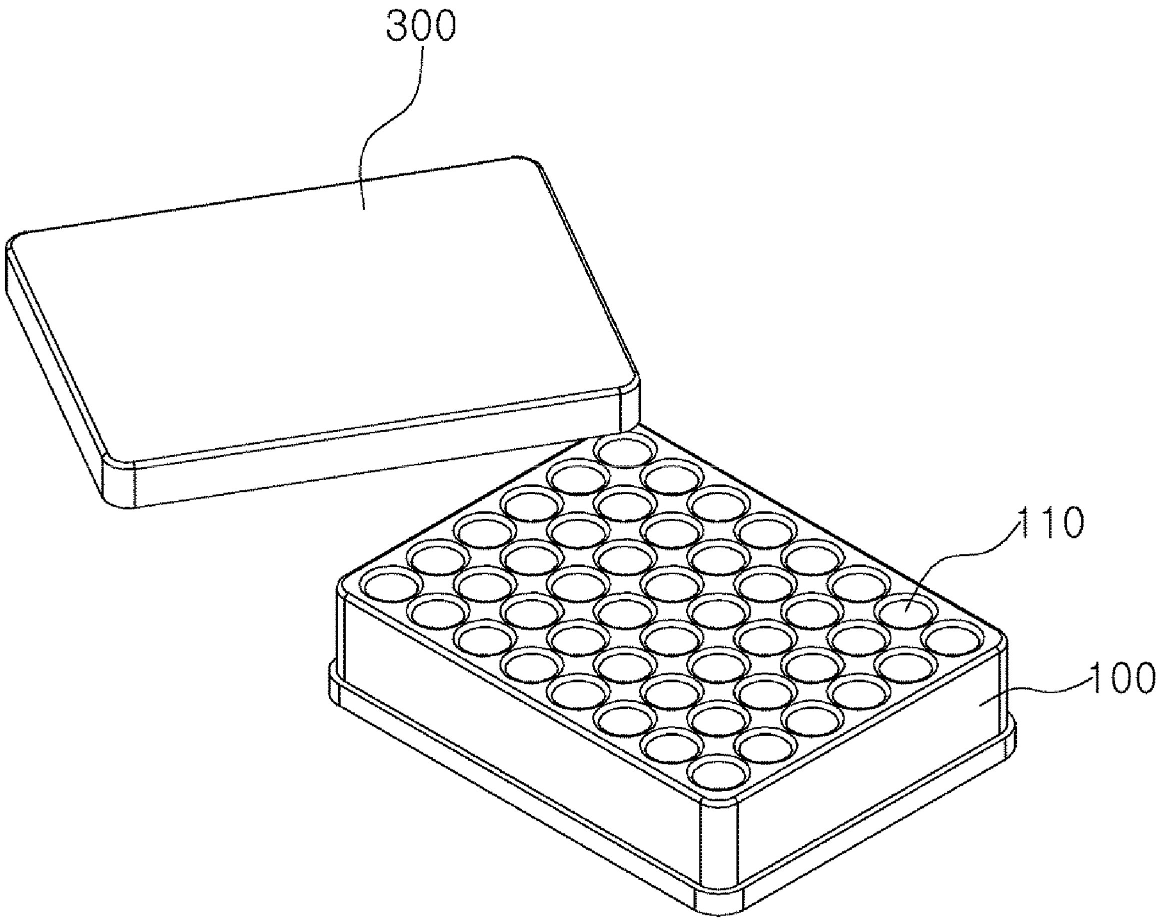
FIG. 10 is an exemplary operation diagram of a protective cover rotating about a point.

In addition, FIG. 9 is an exemplary diagram of an organoid culture device provided with a protective cover; FIG. 10 is an exemplary operation diagram of a protective cover rotating about a point; and FIG. 11 is an exemplary operation diagram of a protective cover rotating about an axis.

Figure 11:
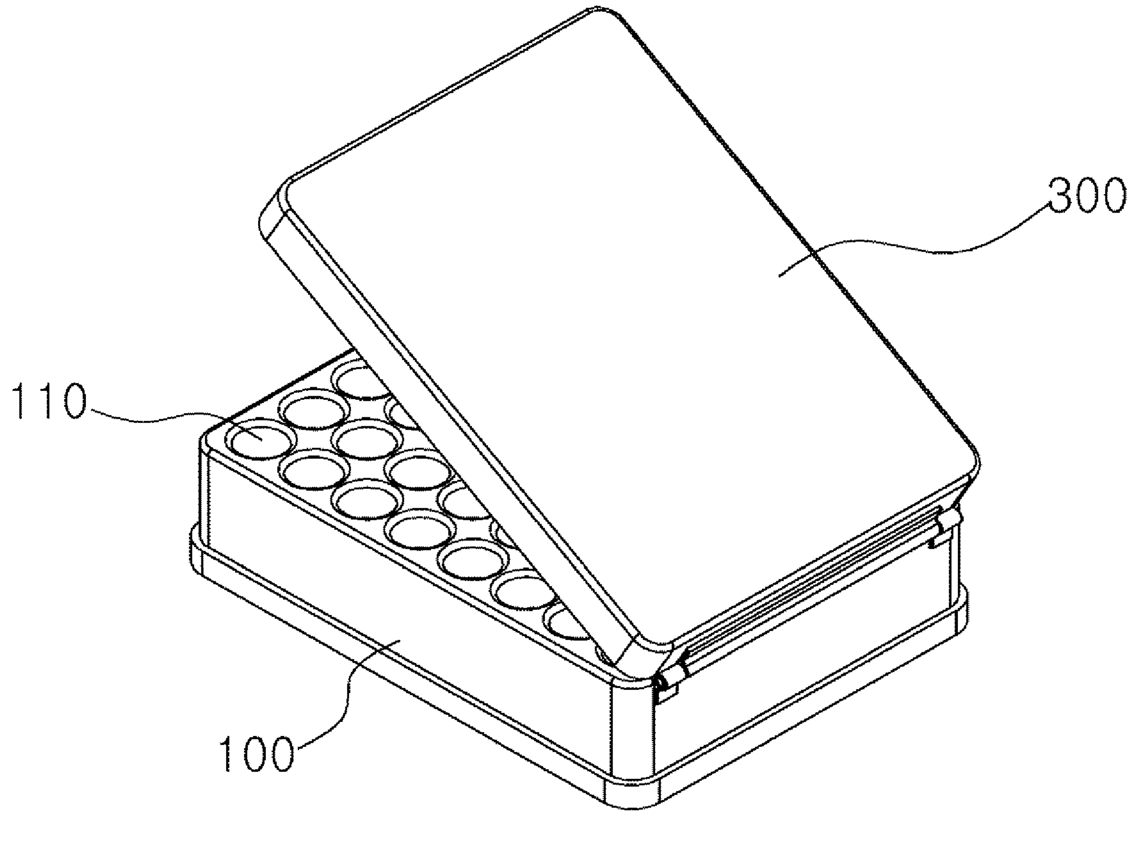
FIG. 11 is an exemplary operation diagram of a protective cover rotating about an axis.

Referring to FIGS. 9 to 11, an organoid culture device 1 according to an embodiment of the present invention may further include a protective cover 300 inserted to culture grooves 210 to protect organoids S being cultured from external shocks or foreign substances such as dust.

Specifically, the protective cover 300 may be formed in the shape of a housing or case covering the top of the organoid device 200.

At this time, the protective cover 300 may be formed to have a height corresponding to the height of the culture plate 100 and thus may be provided in a form that can tightly surround the top and side edges of the culture plate 100. However, it may be formed to have a predetermined height from an upper surface of the culture plate 100, thereby forming a predetermined space inside the protective cover 300.

Meanwhile, the shape of the rectangular box by which the protective cover 300 is illustrated is only a preferred shape, and it may include various cover shapes that can cover the upper portion of the culture plate 100.

Accordingly, an organoid culture device 1 according to an embodiment of the present invention has an advantage that it can protect an organoid S seated and cultured in the culture groove 210 from external shocks or foreign substances by means of a protective cover 300.

Here, as shown in FIG. 11, the protective cover 300 may be provided to rotate about one point of the culture plate 100, or as shown in FIG. 11, it may be provided to rotate about one axis of the culture plate 100.

Accordingly, the protective cover 300 according to an embodiment of the present invention may be operated to selectively open or seal an organoid device 200 according to a user's request.

In addition, the protective cover 300 may be provided with a locking device securing the protective cover 300 to the top of the culture plate 100 after the culture plate 100 is sealed.

Accordingly, a protective cover 300 according to an embodiment of the present invention has an advantage that in moving an organoid culture device 1, it can be moved after being temporarily sealed, enabling more stable operation.

Figure 12:
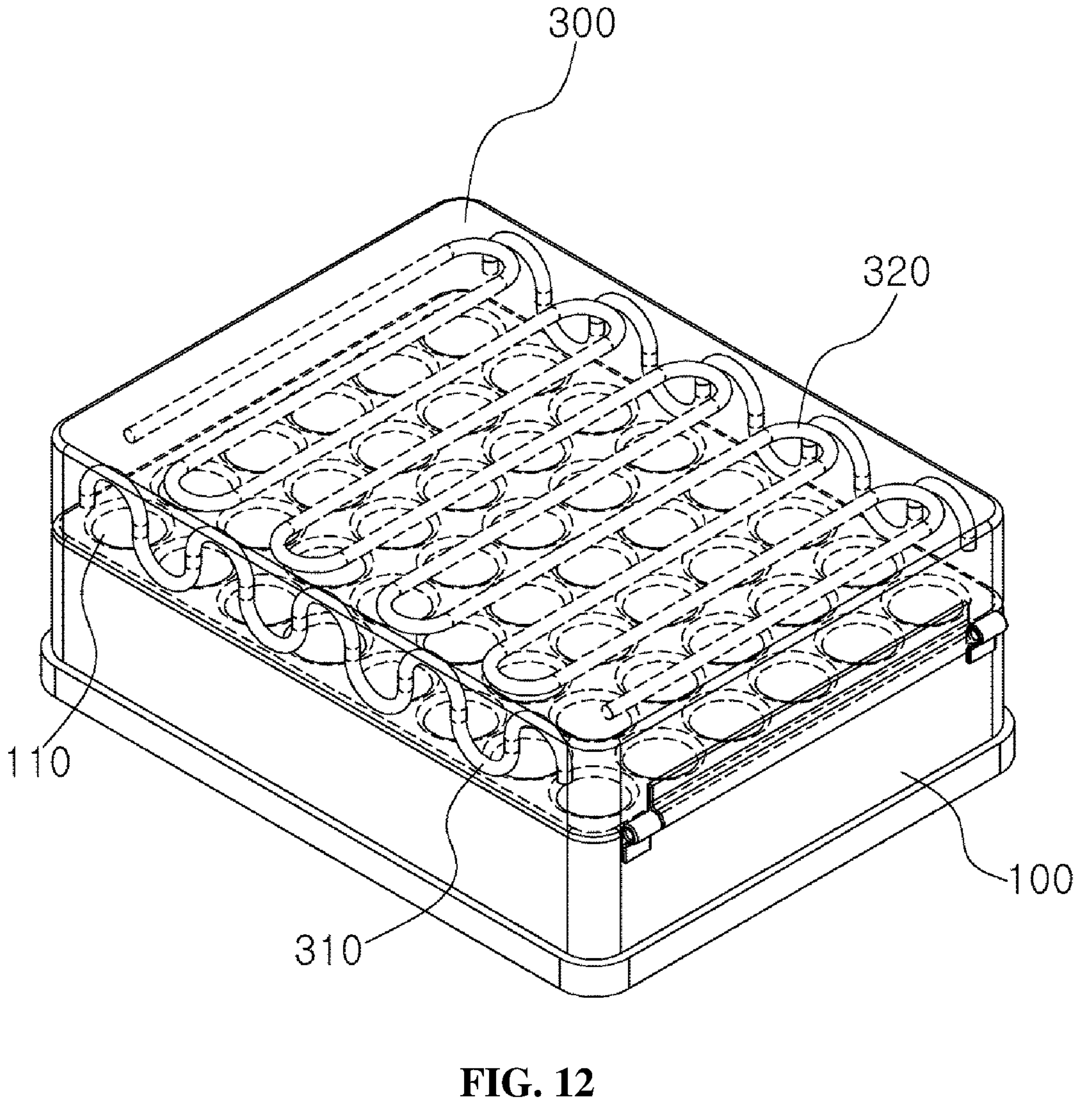
FIG. 12 is an exemplary diagram of a protective cover with an air conditioning flow path formed thereon.

In addition, FIG. 12 is an exemplary diagram of a protective cover with an air conditioning flow path formed thereon.

Referring to FIG. 12, the protective cover 300 according to an embodiment of the present invention may include a first air conditioning flow path 310 and a second air conditioning flow path 320.

Here, the first air conditioning flow path 310 and the second air conditioning flow path 320 may be connected to a separate supply device for supplying a cooling or heating means, which has a predetermined length, which is provided in the shape of a hose through which gas or liquid may flow, and which allows for flow of a cooling or heating means in a gaseous or liquid state for cooling or heating.

Specifically, the first air conditioning flow path 310 may be provided vertically along an inner wall of the protective cover 300, and the second air conditioning flow path 320 may be horizontally positioned on an inner ceiling of the protective cover 300.

At this time, as illustrated in FIG. 12, the first air conditioning flow path 310 and the second air conditioning flow path 320 be provided as a wave pattern, that is, a waveform, along the longitudinal direction of each of the air conditioning flow paths 310, 320, or it may be provided to have a zigzag pattern.

However, the air conditioning flow paths 310, 320 provided in the shape of the waveform are simply a form and an array to increase thermal efficiency by having the maximum area in the inner space of the protective cover 300, and they may be formed to have a straight length rather than a bent form.

Here, the air conditioning flow paths 310, 320 according to an embodiment of the present invention may be most preferably operated to maintain an inner temperature of the protective cover 300 at 35° ° C. to 37° C., which is the temperature range of body temperature which is optimal for growth of organoids S.

As a use example to describe the operation of the protective cover 300 provided with the air conditioning flow paths 310, 320 according to an embodiment of the present invention, first, as a heating means flows in the first air conditioning flow path 310 formed vertically and a cooling means flows in the second air conditioning flow path 320, air ascends on a side of the protective cover 300 and air descends toward the top of the center of the protective cover 300 so that an air convention effect may be derived inside the protective cover to maintain a carbon dioxide concentration within a range of 1% to 5%. Here, the cooling means is not limited to a refrigerant for refrigerant cooling, but may encompass air cooling, oil cooling, water cooling, gas cooling, and any other cooling means that can be appreciated by one of ordinary skill in the art. Accordingly, there is an advantage that the temperature inside the protective cover 300 may be flexibly adjusted.

In summary, an organoid culture device 1 according to an embodiment of the present invention has an advantage of facilitating the culture of organoids S more efficiently by more flexibly adjusting the environment inside the protective cover 300 sealed from the outside, more specifically, the temperature inside the protective cover 300.

Figure 13:
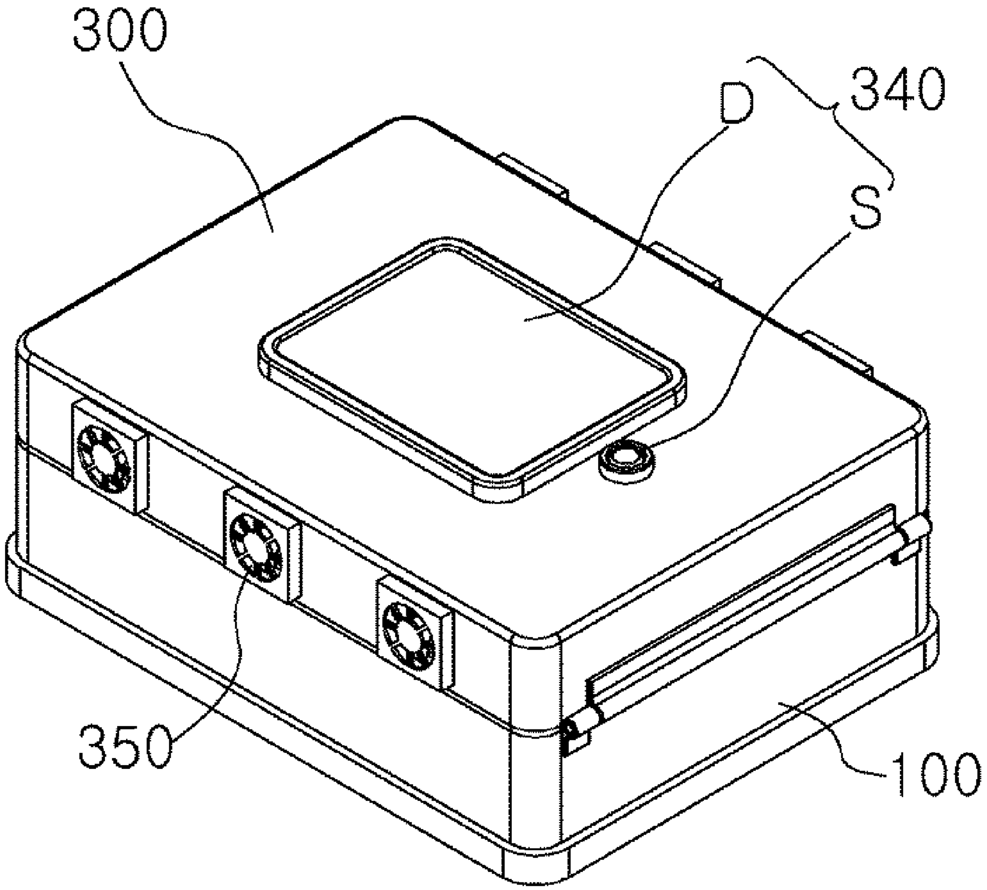
FIGS. 13 and 14 are exemplary diagrams of a protective cover provided with a measurement portion, an input/output device, and an air conditioning device according to an embodiment of the present invention.
Figure 14:
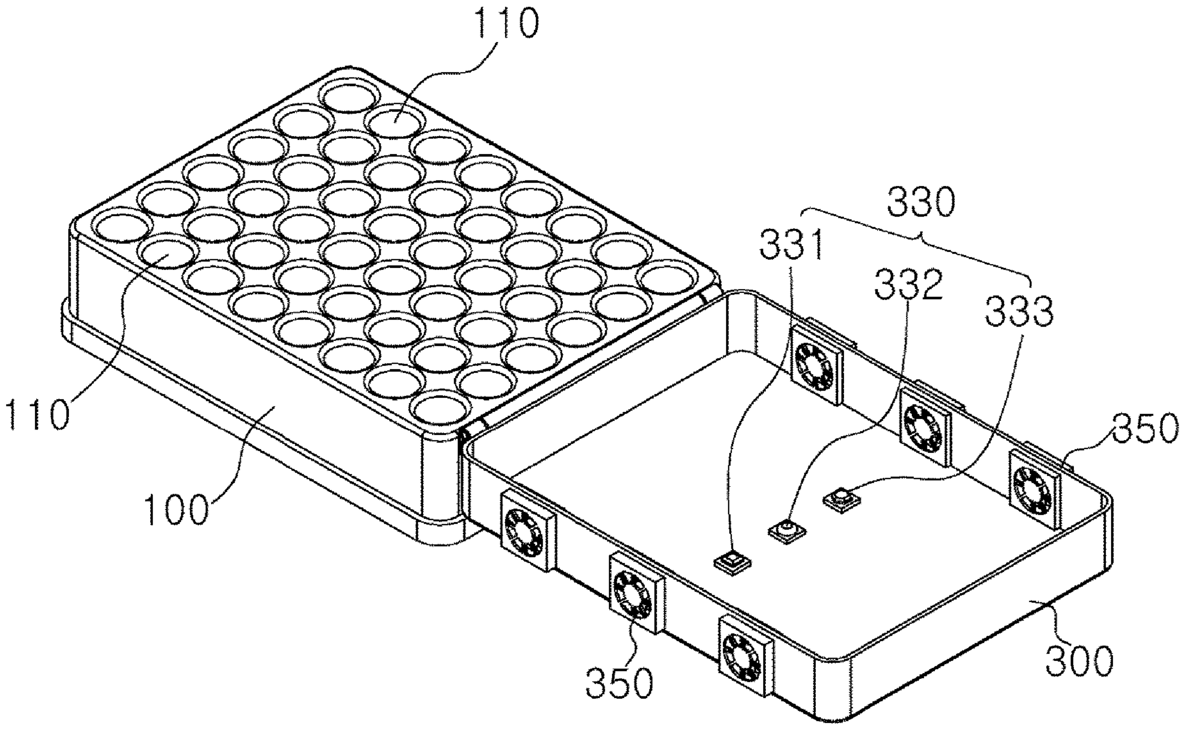

In addition, FIGS. 13 and 14 are exemplary diagrams of a protective cover provided with a measurement portion, an input/output device, and an air conditioning device according to an embodiment of the present invention.

Referring to FIGS. 13 and 14, an organoid culture device 1 according to an embodiment of the present invention may further include a measurement unit 330 and an input/output device 340.

First, the measurement portion 330 may measure a critical state inside the protective cover 300.

Specifically, the measurement portion 330 may include: a humidity measurement sensor 331 provided inside the protective cover 300 and measuring the humidity inside the protective cover 300; a temperature measurement sensor 332 measuring the carbon dioxide concentration inside the protective cover 300; and a carbon dioxide concentration measurement sensor 333 measuring the carbon dioxide concentration inside the protective cover 300.

In addition, the input/output device 340 may receive the critical state value measured through the measurement unit 330 and display it to a user, and it may be provided with the features of a display D and a switch S provided on top of the protective cover 300, as illustrated in FIG. 13.

In addition, the operation of the first air conditioning flow path 310 and the second air conditioning flow path 320 described above may be controlled by receiving user input values through the input/output device 340.

In addition, the input/output device 340 may receive a user's setting value, and when any critical value among temperature, humidity, and amount of ultraviolet rays exceeds the preset value set by the user, it may be provided with an alarming means to notify it to the user by means of sound or light.

Through this, an organoid culture device 1 according to an embodiment of the present invention can obtain real-time information about temperature, humidity, and ultraviolet rays, which are critical values in culturing organoids S, thereby having an advantage of enabling more effective operation in culturing organoids S.

In addition, referring to FIG. 14, a protective cover 300 according to an embodiment of the present invention may be provided with, in addition to the first air conditioning flow path 310 and the second air conditioning flow path 320 described above, an air conditioning device 350 for adjusting the culture environment of organoids S being cultured inside the protective cover 300, more specifically, adjusting the environment inside the protective cover 300 to a temperature of 35° ° C. to 37° C. and a carbon dioxide concentration of 1% to 5%.

Specifically, the air conditioning device 350 may be provided as a blade-rotating fan FAN provided at the top of a side of the protective cover 300, as illustrated in FIG. 14.

In addition, the air conditioning device 350 provided on the protective cover 300 may be provided on the culture plate 100 in the same manner.

Specifically, when the air conditioning device 350 is provided on the culture plate 100 and when air is supplied in a direction of the organoid device 200 through the first air injection port 120 described above, air is supplied into the second air injection port 220 provided in the organoid device 200, thereby having an advantage of instantaneously and quickly eliminating excessively generated bubbles.

Meanwhile, a rotating fan (FAN) illustrated in the drawing is an expression to represent a schematic configuration of an air conditioning device to aid understanding of the present invention, and any air conditioning means and device for causing a flow of the air inside the protective cover 300 to the inside or to the outside may be used.

Figure 15:
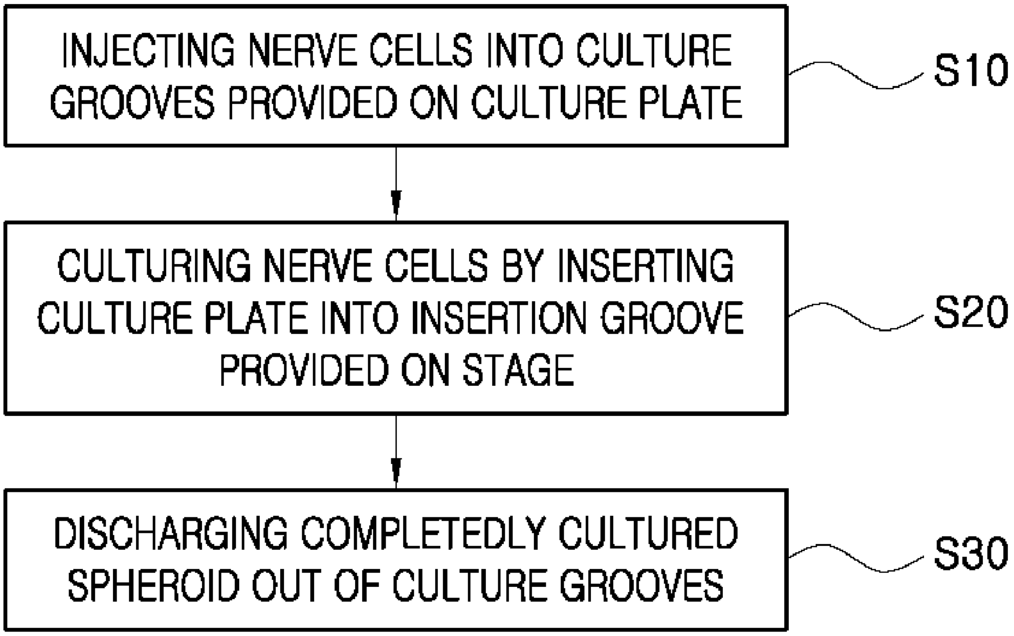
FIG. 15 is a flowchart of an organoid culture method using an organoid culture device according to an embodiment of the present invention.

In addition, FIG. 15 is a flowchart of an organoid culture method using an organoid culture device according to an embodiment of the present invention; and FIG. 16 is an exemplary diagram showing an organoid of a 3D shape cultured through an organoid culture device and an organoid culture method using the same according to an embodiment of the present invention.

Referring to FIG. 15, in the culture method for culturing an organoid of a 3D shape using an organoid culture device according to an embodiment of the present invention, culturing of organoids may be performed by an injection step S10, a culture step S20, and a completion step S30.

Here, the organoid may include any cells used to culture an organoid S, such as primary cell line, continuous cell line, stem cells, tumor cells, immunocytes, bacteria, and microorganisms.

First, in the injection step S10, cells may be injected into an culture groove provided in an organoid device.

Next, in the culture step S20, an organoid device may be inserted into an insertion groove provided on a culture plate to culture the cells.

In addition, in the completion step S30, the culture may be completed and the completely cultured organoids may be discharged to the outside of the culture groove.

Accordingly, an organoid culture method according to an embodiment of the present invention has an advantage that the operation may be easier compared to the conventional organoid culture devices.

Although a 3D organoid culture device 1 according to an embodiment of the present invention and an organoid culture method using the same have been described above in detail with reference to FIGS. 1 to 16, the scope of the present invention is not limited thereto. Rather, various modifications and improvements made by those skilled in the art using the basic concept of the present invention defined in the following claims also fall within the scope of the present invention.

The invention claimed is:

1. An organoid culture device to culture organoids in a 3D shape, comprising:

a culture plate including one or more insertion grooves; and an organoid device configured to be inserted to and removed from each of the one or more insertion grooves, and including one or more culture grooves, wherein the one or more culture grooves are disposed on a surface of the organoid device in a pattern having a diameter of 5 μm to 5000 μm and spaced apart from each other in 5 μm to 5000 μm, and wherein below each of the one or more insertion grooves, a first air injection port is disposed to discharge the organoid device out of each of the one or more insertion grooves by supplying air in a direction of the inserted organoid device.

2. The organoid culture device according to claim 1, wherein, below each of the one or more culture grooves, a second air injection port is disposed to discharge an organoid out of each of the one or more culture grooves by delivering air in a direction of the organoid after receiving the air from the first air injection port.

3. The organoid culture device according to claim 1, wherein a heater for generating heat is provided inside the culture plate along an outer circumference of each of the one or more insertion grooves.

4. The organoid culture device according to claim 1, further comprising:

a protective cover protecting the organoids seated and cultured in the one or more culture grooves from external shocks or foreign substances, wherein the protective cover is configured to be detachable from or attachable to an upper portion of the culture plate or to rotate about a point or an axis of the culture plate, thereby operating to selectively open or seal the upper portion of the culture plate.

5. The organoid culture device according to claim 4, wherein the protective cover includes:

a first air conditioning flow path disposed vertically on an inner wall of the protective cover to allow a cooling means or a heating means to flow therein; and a second air conditioning flow path disposed on an inner ceiling of the protective cover to allow the cooling means or the heating means to flow therein.

6. The organoid culture device according to claim 4, further comprising:

a measurement portion including a sensor for measuring a critical state inside the protective cover; and an input/output device including a display, receiving the critical state measured by the measurement portion, displaying the critical state to a user, and receiving an input value from the user.

7. An organoid culture method for culturing the organoids in the 3D shape, using the organoid culture device according to claim 1, comprising:

injecting cells into the one or more culture grooves in the organoid device;

culturing the cells by inserting the organoid device into an insertion groove provided on the culture plate; and discharging the cultured organoids to an outside of the one or more culture grooves after the culturing is completed.

* * * * *